United States Patent [19]

Kluender

[11] 4,158,018

[45] Jun. 12, 1979

[54] 3-OXA CARBINOL PROSTAGLANDIN ANALOGS

[75] Inventor: Harold C. Kluender, Madison, Wis.

[73] Assignee: Miles Laboratories, Inc., Elkhart, Ind.

[21] Appl. No.: 941,746

[22] Filed: Sep. 12, 1978

[51] Int. Cl.$^2$ ............................................. C07C 177/00
[52] U.S. Cl. ................................. 260/586 R; 424/331
[58] Field of Search ..................................... 260/586 R

[56] References Cited

U.S. PATENT DOCUMENTS 3,636,120  1/1972  Pike ................................. 260/586 R

FOREIGN PATENT DOCUMENTS 2236834  1/1974  France.

Primary Examiner—Gerald A. Schwartz
Attorney, Agent, or Firm—Jerome L. Jeffers

[57] ABSTRACT

Disclosed are trans, 3-oxa carbinol analogs of prostaglandin $E_1$ represented by the formula:

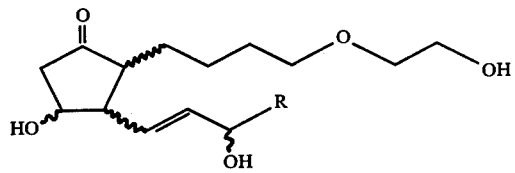

wherein R is n-alkyl of 4–6 carbon atoms, cycloalkyl of 5 to 7 carbon atoms or 1,1-dimethylalkyl of 6 to 8 carbon atoms. Particular compounds corresponding to the above formula are variously useful as antithrombotic agents due to their ability to inhibit platelet aggregation, bronchodilators, inhibitors of gastric secretion and antihypertensive agents.

12 Claims, No Drawings

3-OXA CARBINOL PROSTAGLANDIN ANALOGS

BACKGROUND OF THE INVENTION

1. Field of the Invention

The compounds of this invention are analogues of natural prostaglandins.

Natural prostaglandins are salicyclic compounds related to prostanoic acid, the structure of which is:

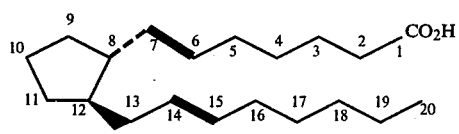
(I)

By convention, the carbon atoms of I are numbered sequentially from the carboxylic carbon atom. An important stereochemical feature of I is the trans-orientation of the sidechains $C_1$–$C_7$ and $C_{13}$–$C_{20}$, an orientation common to all prostaglandins. In I, as elsewhere in this specification, solid lines (━) provide a reference plane (such as the cyclopentyl ring or the bonds among $C_1$–$C_7$ and $C_{13}$–$C_{20}$); a dashed line (--) indicates projection of a covalent bond below such reference plane (alpha-configuration); while a wedged line (◂) represents direction above such plane (beta-configuration). These conventions apply to all structural formulae subsequently discussed in this specification. In some structures, however, a swung dash or serpentine line (∿) denotes orientation of a covalent bond either above or below the plane of reference (indicated by the Greek letter xi in the nomenclature of such structures).

Natural prostaglandins have the general structure,

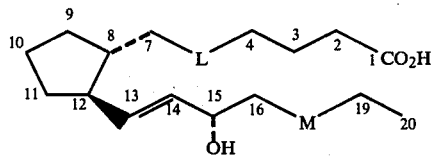
(II)

in which L and M may be ethylene or cis-vinylene radicals. Prostaglandins are characterized by the substituents on the cyclopentyl ring, the position of double bonds, if any, in the cyclopentyl ring and the number of double bonds in the side chains. When the cyclopentyl ring is fully saturated, carbonyl substituted at the 9-position and hydroxyl substituted at the 11-position an E-class prostaglandin is represented (PGE) and when there is a single double bond in the sidechains, i.e., L and M in formula II are ethylene, a type-1 prostaglandin is represented. The naturally occurring E-class type 1 prostaglandins known as prostaglandin $E_1$ or $PGE_1$, is represented by the formula:

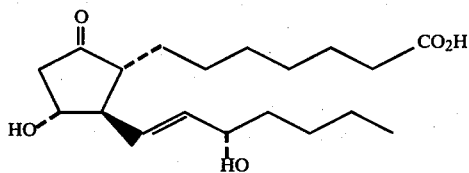
(III)

Formulae I, II and III depict the nat-isomer, i.e., the $C_7$–$C_8$ bond in the alpha configuration and the $C_{12}$–$C_{13}$ bond in the beta-configuration. In the ent-isomer (which does not occur in nature), the direction of the bonds at $C_7$–$C_8$ and $C_{12}$–$C_{13}$ is reversed.

Recent research indicates that certain prostaglandins, including $PGE_1$ and analogues thereof, elicit biochemical and physiological effects in a variety of mammalian systems. For example, in rats $PGE_1$ increases the release of growth hormone and in sheep it has been found to inhibit ovarian progesterone secretion. In mice, $PGE_1$ has been found to increase thyroid activity whereas in hypophysectomized rats it has been found to stimulate stereodogenesis in the adrenal glands.

In the mammalian male reproductive system, $PGE_1$ contracts the smooth muscle of the vas deferens and in the female reproductive system PGE compounds contract uterine smooth muscle. Prostaglandins stimulate contraction of gastrointestinal smooth muscle in vivo and in vitro. In dogs, $PGE_1$ inhibits gastric secretion. In most mammalian respiratory tracts, PGE compounds affect in vitro preparations of tracheal smooth muscle. The human lung normally contains PGE compounds; consequently, some cases of broncial asthma may involve an imbalance in the production or metabolism of these compounds.

In addition, prostaglandins are involved in certain hematic mechanisms in mammals. For example, $PGE_1$ inhibits aggregation of blood platelets in vitro. In a variety of mammalian cardiovascular systems, PGE compounds are vasodilators by virtue of their action or vascular smooth muscle.

Accordingly, it can be seen that prostaglandins and their analogues have broad clinical implications and research in this area continues in laboratories throughout the world.

PRIOR ART

Prior art relevant to the 3-oxa carbinol prostaglandin analogues disclosed and claimed herein is disclosed in French Pat. No. 2,236,834 published Jan. 10, 1974 (U.S. application Ser. No. 332,067) assigned to the Upjohn Co. This reference is directed to 3- and 4-oxa prostaglandin analogues which are acids or esters represented by the generic formula:

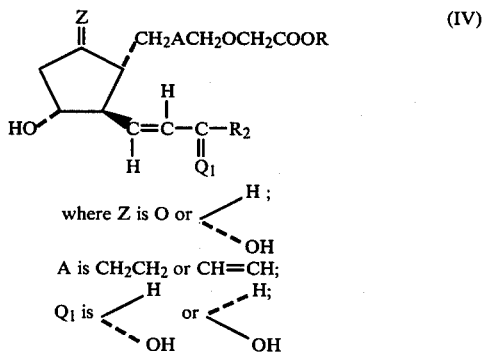
(IV)

R is H, 1–8 carbon alkyl, 3–10 carbon cycloalkyl, 7–12 carbon aryalkyl or phenyl optionally substituted by 1–3 chloro or 1–4 carbon alkyl groups; $R_2$ is —$CHR_4(CH_2)_gCH_3$; $R_4$ is H or F and g is 1–5.

It should be noted that all of the compounds described in this disclosure are acids and esters whereas all of the compounds claimed herein are C-1 carbinol analogues. It is also noted that in none of these prior art compounds is $R_2$ tertiary alkyl or cycloalkyl. In the instantly claimed compounds $R_2$ may be tertiary alkyl, e.g., 1,1-dimethyl pentyl or cycloalkyl, e.g., cyclohexyl as well as n-alkyl, e.g., n-pentyl.

Other references which disclose 4 or 5-oxoprostaglandins are U.S. Pat. No. 3,920,723 and U.S. Pat. No. 3,864,387. Both of these disclosures again describe only acids and esters.

Prostaglandins of the $E_1$ type having a carbinol group at the 1-position are known. For example, U.S. Pat. No. 3,636,120 discloses 1, 11α, 15 S-trihydroxyprost-13E-en-9-one of the formula:

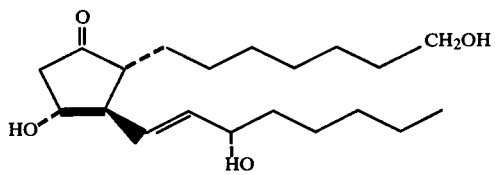

While this compound is carbinol substituted at the 1-position, it contains no oxa group in the interior of the upper chain.

Compounds of the type set out in formula IV, i.e., 3-oxa prostaglandins, are resistant to the normal 3-oxidation observed in prostaglandin metabolism to produce inactive metabolites while carbinol prostaglandins are known to be quite selective in their biological activities and hence have desirable high therapeutic indexes. In the present invention these two elements are combined in a single analog which should exhibit the resistance to metabolism associated with 3-oxa analogs and also the selectivity of activity associated with carbinol analogs.

SUMMARY OF THE INVENTION

The present invention involves trans, 3-oxa carbinol analogs of prostaglandin $E_1$ having the structural formula:

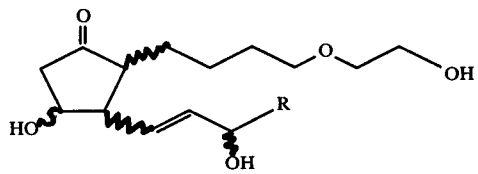

In the above formula R is n-alkyl of 4 to 6 carbon atoms, cycloalkyl of 5 to 7 carbon atoms or 1,1-dimethylalkyl of 6 to 8 carbon atoms.

These compounds are prepared by reacting an organolithiocuprate of the formula:

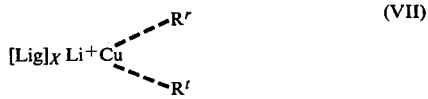

wherein:
Lig is tri-(di-alkylamino)phosphine of 6-12 carbon atoms, trialkylphosphine of 3-13 carbon atoms, diarylphosphine, dialkylsulfide of 4-8 carbon atoms, arylsulfide or di-(trialkylsilyl) amino having 6-12 carbon atoms;
$R^r$ is iodide, thiophenylate, $R^t$ or alkyn-1-yl having 3-8 carbon atoms;
X is 1 or 2; and
$R^t$ is a radical having the formula:

wherein R is as defined as above and $R_3$ is trialkylsilyl of 3-6 carbon atoms or 1-alkoxyalkyl of 2-6 carbon atoms or tetrahydropyran-2-yl with a compound having the formula:

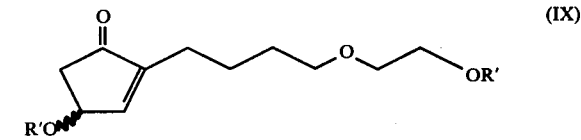

wherein R' is the same as $R^3$ to form:

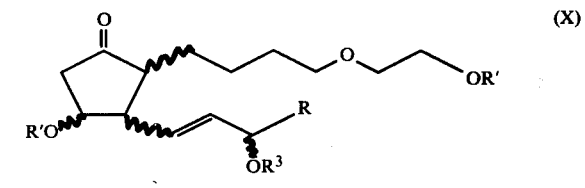

and;
treating the intermediate material X with a weak acid such as aqueous acetic or formic acid to convert the R' and $R^3$ groups to H to thereby form the desired product.

Also disclosed herein are key intermediate materials IX and X and the process for their preparation.

DETAILED DESCRIPTION AND PREFERRED EMBODIMENTS

The syntheses of the compounds of this invention are shown in Schemes I to III, infra. Scheme I depicts the synthesis of key intermediate (12), i.e., IX above, starting with commercial octadiene (1) and 2-bromoethanol (3), In Scheme II commercially available starting materials isobutyric acid (21) or a variety of commercial acid chlorides (26) are converted in a sequence of steps to another key intermediate (13) or (13*) [* the optically active form of (13)]. In Scheme III the key intermediates (12) and (13) or (13*) are joined via an organo copper reagent to form the instantly claimed compounds (19) and (20). The use of similar organocopper reagents in the preparation of prostaglandins is well known in the literature [see for example C. J. Sih, et al., J. Amer. Chem. Soc., 97, 857 and 865 (1975) and references cited therein, also E. J. Corey and D. J. Beames, J. Amer. Chem. Soc., 94, 7210 (1972)].

According to Scheme I, octadiene is reacted with one equivalent of ozone in a suitable solvent such as methanol, ethanol or the like at from −80° to 0° C. and in turn is reacted with sodium borohydride without isolation of the intermediate ozonide. The product is hept-6-en-1-ol (2). Diaper and Mitchell, Can. J. Chem., 38, 1976 (1960) describe a similar sequence to obtain a primary alcohol from a terminal alkene.

Using techniques well known to those skilled in the art, 2-bromoethanol (3) is converted to its THP derivative (4) by reaction with commercial dihydropyran in a suitable solvent such as ether or methylene chloride or the like at from −20° to ambient temperature in the presence of an acid catalyst such as p-toluenesulfonic acid or phosphorous oxychloride. It was found that frequently this reaction occurred spontaneously without added catalyst, most likely the result of hydrobromic acid contamination in the commercial 2-bromoethanol used. The reaction is conveniently monitored for completion by ir analysis of removed aliquots. Disappearance of the broad OH band at 3200-3600 cm$^{-1}$ is used for this analysis.

A classical Williamson coupling of (2) and (4) in the presence of sodium hydride in a suitable solvent such as dry tetrahydrofuran at from −20° to reflux yields ether (5).

Reaction of (5) with mercuric acetate in water/tetrahydrofuran followed by basic aqueous sodium borohydride treatment results in Markownkov hydration of the olefin of (5) to yield alcohol (6). The techniques described by H. C. Brown and P. Geoghegan, Jr., *J. Amer. Chem. Soc.*, 89, 1522 (1967) were used.

A classical Jones reaction of alcohol (6) yielded ketone (7) following the techniques of C. Djerassi, et al, *J. Org. Chem.*, 21, 1547 (1956). Other reagents suitable for this transformation also include, but are not limited to, various chromium trioxidepyridine reagents such as those of J. C. Collins, et al, *Tetrahedron Letters*, 3363 (1968) and E. J. Corey and J. W. Suggs, *Tetrahedron Letters*, 2647 (1975).

Ketone (7) was condensed with diethyloxalate in ethanol using sodium ethoxide catalysis to form an intermediate oxalyl containing intermediate which on hydrolysis yielded substituted cyclopentan-1,3,4-trione (8). The condensation is conducted at between −20° C. and solvent reflux, and can be conducted in any number of alcoholic solvents in the presence of their respective sodium salts as catalyst. The salt is conveniently generated by adding sodium metal to anhydrous alcohol under an inert atmosphere such as argon or nitrogen. Methanol, ethanol, isopropanol or benzyl alcohol can all be used. The intermediate can be isolated or, preferentially, hydrolyzed directly by adding aqueous acid such as hydrochloric or aqueous base such as sodium bicarbonate to the reaction mixture after condensation of (7) with the dialkyloxalate. The hydrolysis can be conducted at between 0° and the reflux temperature of the solvent used. If base is used, the product initially obtained is (8), whereas if acid is used, the product is (9). If (8) is first obtained, it can be converted to (9) by treatment with aqueous acid, such as acetic or hydrochloric acid and water. The conversion of ketone (7) to trione (8) is similar to that first described by J. Katsube and M. Matusi, *Agr. Biol. Chem.*, 33, 1078 (1969), and since used by many including Sih et al, *J. Amer. Chem. Soc.*, 97, 857, 865 (1975) and Kluender and Peruzzotti, *Tetrahedron Letters*, 2063 (1977) for the synthesis of natural and analog prostaglandins.

Trione (9) was reacted with 1 atmosphere of hydrogen in isopropanol over 5% Pd on carbon to yield hydroxydione (10) following the general procedure of P. Collins, et al, *Israel J. of Chem.*, 6, 839 (1968) which was used for a similar substituted cyclopentanetrione to hydroxycyclopentanedione conversion.

Intermediate (10) was converted to (11) in a sequence of steps which started with reaction of (10) with mesitylenesulfonyl chloride in a suitable solvent such as tetrahydrofuran or ether in the presence of a base such as triethylamine or pyridine at from −20° C. to ambient temperature. The first formed intermediate may be isolated, or preferentially the crude product reaction mixture is treated directly with a reducing agent such as sodium bis(2-methoxyethoxy)aluminum hydride or sodium borohydride in a solvent compatible with the reducing agent such as ether or THF with the first reagent or alcohol with sodium borohydride at from −80° to ambient temperature. The second formed intermediate is then isolated by techniques well known to those skilled in the art and then treated for several hours with a mixture of sodium oxalate and oxalic acid in chloroform with or without added alcohol such as methanol or ethanol (ca. 10%). Addition of such an alcohol suppresses formation of oxalate ester side products of desired product (11). The product (11) is then isolated by standard techniques and is purified by chromatography. The conversion of (10) to (11) parallels those methods described by Sih et al., and Kluender and Peruzzotti (references given above).

The hydroxy groups of (11) are blocked as their tetrahydropyranyl, trialkylsilyl or 1-alkoxyalkyl ethers to form (12) using methods well known to those skilled in the art (see Kluender and Peruzzotti for a very similar transformation).

According to Scheme II isobutyric acid (21) is reacted with two equivalents of a strong base such as lithium diisopropylamide in an inert solvent such as dry THF followed by reaction with 1-iodo or 1-bromo propane, butane or pentane at −20° C. to ambient temperature to yield alkylated acid (22). This is the method of P. L. Cregar, *J. Amer. Chem. Soc.*, 89, 2500 (1967), later given in *Organic Synthesis*, 50, 58 (1970).

Methyl ketone (23) is then reacted with methylformate and sodium hydride in a suitable solvent such as dry ether or THF at between −20° C. and solvent reflux temperature to yield formylated intermediate (24). Other formate esters such as ethyl or isopropyl formate may be used in lieu of methyl formate. A small amount of alcohol such as dry methanol or dry ethanol is helpful as a catalyst in this reaction.

Intermediate (24) is then reacted with an alkyl or arylsulfonyl chloride such as p-toluenesulfonyl chloride or methanesulfonyl chloride in the presence of a tertiary amine base such as pyridine or triethyl amine or the like in an inert solvent such as dry ether or dry THF at from −20° to ambient temperature to yield enol alkyl or arylsulfonate (25) wherein X is alkyl or arylsulfonate and $R^2$ is 1,1-dimethylpentyl. Alternately (24) may be reacted with a chlorinating agent such as thionyl chloride to yield (25) wherein X is chloro, or with a brominating agent such as phosphorous tribromide to yield (25) wherein X is bromo.

Various acid chlorides (26), wherein $R^2$ is various alkyl or cycloalkyl such as n-pentyl or cyclohexyl or isopropyl [the acid chloride of (21)] are reacted with acetylene in the presence of a Lewis acid such as aluminum chloride in an appropriate solvent such as carbontetrachloride, methylene chloride or chloroform to yield (25) wherein X is chloro. The route (26) to (25) works preferentially when $R^2$ is primary or secondary alkyl and the route (21) to (25) via (24) when $R^2$ is tertiary alkyl. This method of conversion of (26) to (25) when $R^2$ is n-pentyl was described by E. J. Corey and D. J. Beames, *J. Amer. Chem. Soc.*, 94, 7210 (1972).

Intermediate (25) is reacted with a soluble iodide salt such as sodium iodide or lithium iodide in a suitable solvent such as acetone at from ambient temperature to solvent reflux to yield iodo-vinyl, intermediate (27). A small amount of concentrated sulfuric acid may be added as catalyst in the conversion of (25) to (27). This reaction wherein R² is n-pentyl was also described by Corey and Beames.

The ketone function of compound (27) is then reduced to an alcohol of (28) by the use of a hydride reducing agent such as sodium borohydride in ethanol or methanol at between −20° and ambient temperature or by the use of lithium aluminum hydride or the like in ether or THF.

Alcohol (28) may be optionally resolved using classical techniques to yield the structure of natural stereochemistry as shown in structure (29). Such a resolution of (28) wherein R² is n-pentyl has been described by A. F. Kluge et al, *J. Amer. Chem. Soc.*, 94, 7827 (1972).

Either (28) or (29) is then blocked with a suitable blocking agent such as chloromethyl ether (see A. F. Kluge et al) or ethylvinyl ether (see Sih et al) or dihydropyran (see Kluender and Peruzzotti) in a suitable solvent such as ether or THF or methylene chloride in the presence of a catalyst such as p-toluenesulfonic acid or phosphorousoxychloride or with a blocking agent such as t-butyldimethylsily chloride [see C. J. Sih et al, *J. Amer. Chem. Soc.*, 95, 1676 (1973)] or triphenylmethylchloride [see K. T. Bervody and M. J. Weiss, *Prostaglandins*, 3, 505 (1973)] in the presence of a catalyst such as pyridine, triethylamine or imidazole to yield (13) or optically active (13*) if (29) is used.

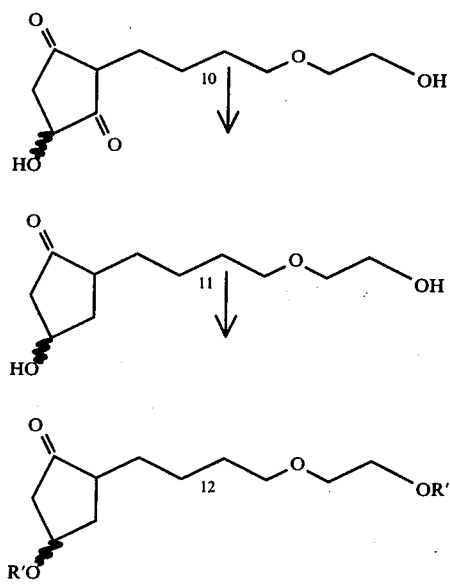

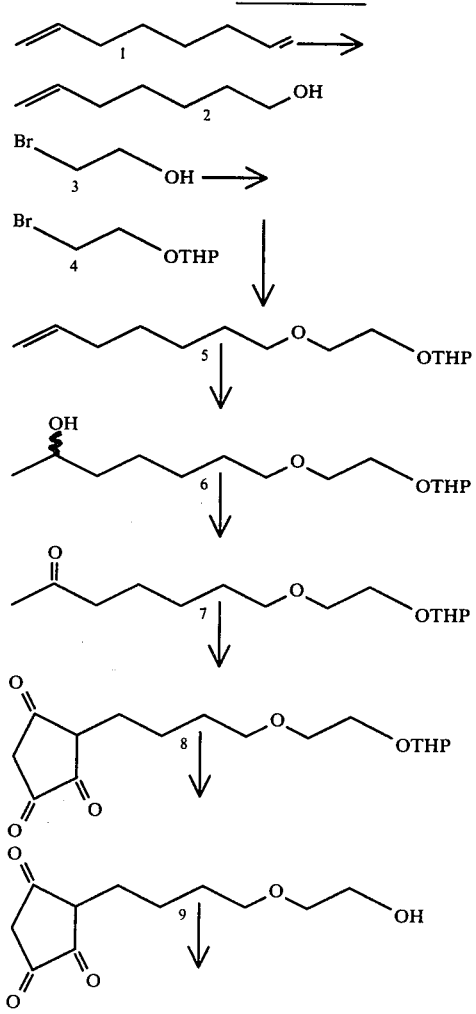

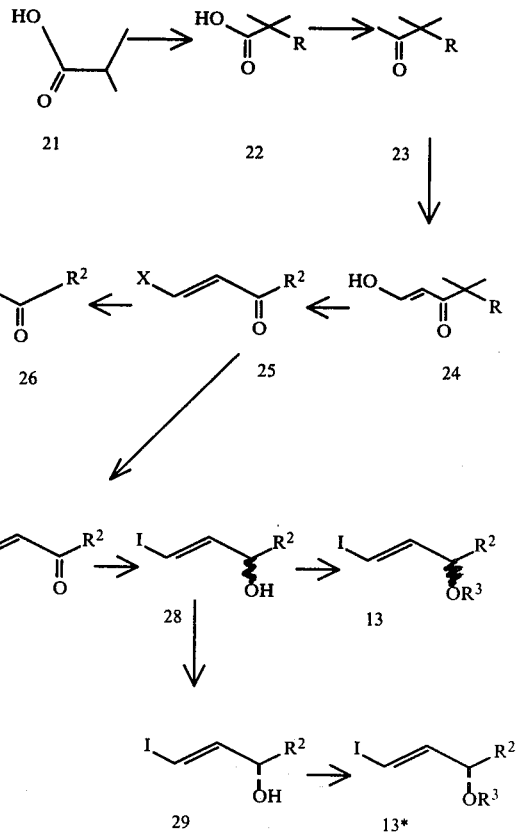

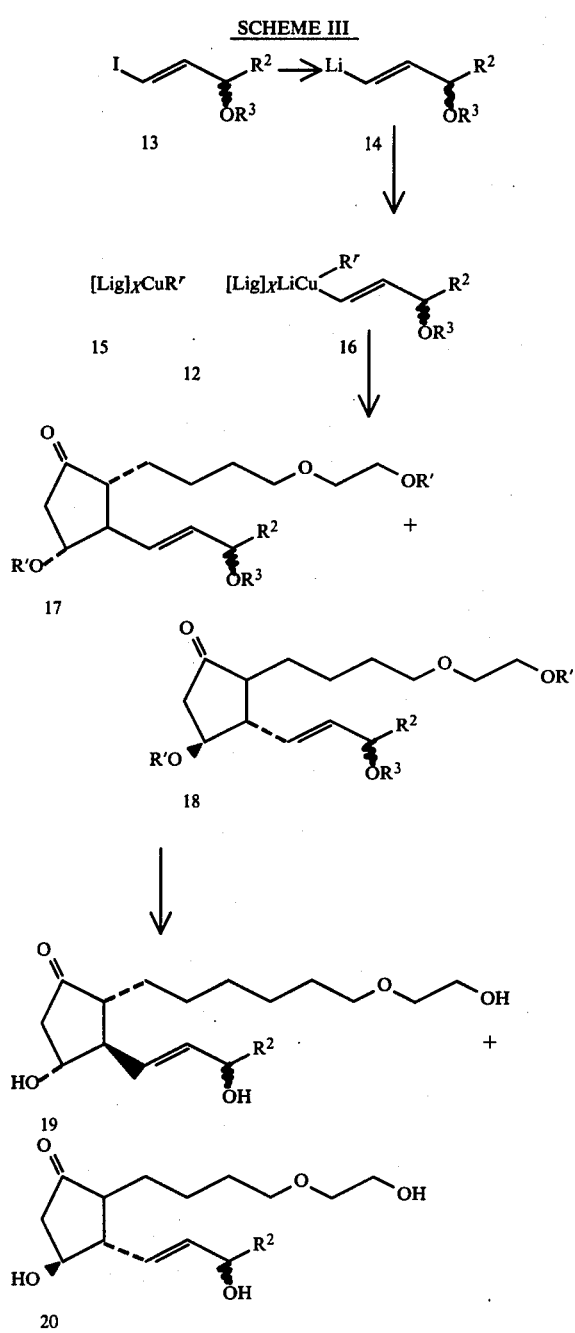

SCHEME III

The method of preparing the prostaglandins of the present invention is further illustrated by the following examples.

In the following examples, the integers in parenthesis are correlated to the various structural formulae in schemes I–III.

EXAMPLE I

Preparation of Hept-6-en-1-ol. (2)

A 55.1 g (0.50 mol) portion of commercial 1,7-octadiene (1) was dissolved in 1 liter of dry methanol. The resultant solution was stirred at −78° as a stream of ozone in oxygen was bubbled in through a gas dispersion tube. The ozone was generated from a stream of dry oxygen using a Welsbach model T-816 ozone generator set at 115 V, 8 P.S.I. and 2.85 liters/min. which should have delivered ozone at ca 12 g (0.25 mol) per hour. Ozone was thus added to the reaction flask for 2.0 hours to total 24 g (0.50 mol).

The −78° C. cooling bath was removed from the reaction flask and replaced with an ice/water 0° C. bath. After the internal temperature of the reaction mixture had warmed to ca. 0°, a 40 g (1.06 mol) total of sodium borohydride was added over 0.5 hour in several small portions in an attempt to use the ice bath to keep the reaction pot cool. At one point addition of too large a portion resulted in brief warming of the reaction mixture. After all of the sodium borohydride was added, the reaction mixture was stirred a few minutes with ice bath cooling and then condensed by evaporation in vacuo to remove most of the solvent. The resultant residue was mixed with water whereupon the wash solution was back extracted with ether. The combined extract was dried ($MgSO_4$), evaporated at 20 mm at a temperature less than 30° C., and finally distilled at 20 mm. The yield of (2) was 14.5 g, bp 72°–75°; tlc (ether) $R_f$ 0.48; tlc ($CHCl_3$) $R_f$ 0.11; nmr ($CDCl_3$) δ 1.2–2.2 (7H, m), 3.7 (2H, broad t, J=6.0 Hz), 4.8–5.3 (2H, m) and 5.5–6.3 ppm (1H, m); ir (film) 900, 985, 1050, 1410, 1640, 2850, 2930 and 3200–3600 cm$^{-1}$.

EXAMPLE II

Preparation of 2-Bromo-1-(tetrahydropyran-2-yloxy)ethane(4)

A solution of 37.5 g (0.30 mol) of 2-bromoethanol (3) in 200 ml of dry ether was stirred under argon with ice bath cooling as 36.5 ml (0.40 mol) of dihydropyran was added followed by ca. 50 mg of toluenesulfonic acid. After 1 hour the reaction mixture was washed with saturated aqueous sodium bicarbonate solution, dried ($K_2CO_3$) and then evaporated in vacuo over a few crystals of anhydrous $K_2CO_3$ to yield 65 g of the desired product (4) which was stored cold over $K_2CO_3$ and then decanted when used; tlc ($CHCl_3$) $R_f$ 0.30; ir (film) 810, 870, 960, 1030, 1075, 1120, 1200, 2880 and 2950 cm$^{-1}$.

EXAMPLE III

Preparation of 3-Oxo-1-(tetrahydropyran-2-yloxy)dec-9-one (5)

A 5.8 g (120 mmol) portion of sodium hydride (50% in oil) was rinsed under argon with hexane to remove the oil and then dispersed with stirring in 40 ml of dry THF. A solution of 23.0 g (110 mmol) of 2-bromo-1-(tetrahydropyran-2-yloxy)ethane in 20 ml of dry THF was then added dropwise to the reaction pot as it was stirred under argon. Next a solution of 11.4 g (100 mmol) of hept-6-en-1-ol in 40 ml of THF was added dropwise to the stirred reaction mixture. Quite a bit of gas evolution was observed as the mixture warmed slightly. The resultant mixture was stirred overnight at ambient temperature (ca. 22° C.). A tlc ($CHCl_3$) analysis of the reaction mixture at this point showed the product at $R_f$ 0.18, but also substantial starting material (2) at $R_f$ 0.11 with only a trace of starting material (4) at $R_f$ 0.30. A large side product showed at $R_f$ 0.40 and it was concluded that a significant portion of (4) had decomposed to give the $R_f$ 0.40 side product rather than react with (2) to give the desired product (5). Another 10 g (48 mmol) portion of (4) was added to the reaction pot along with 3.0 g (62 mmol) of unrinsed sodium hydride (50% in oil) whereupon the resultant mixture was refluxed for 2 hours. At this point, the analysis of the reaction mixture showed a better ratio of product (5) to starting material (2), but some (2) still remained. The reaction mixture was quenched by the dropwise addition of water whereupon most of the THF was removed by partial evaporation in vacuo and the remaining aqueous residue was extracted with ether several times. The combined extract was dried (MgSO$_4$) and evaporated in vacuo at which point the resultant residue was distilled at ca. 1 mm to remove a volatile (bp ca. ambient) material which was collected in an ice cooled receiving flask. The 16.4 g of volatile material appeared to be a mixture of starting material (2) and side product R$_f$0.40. The undistilled material was then distilled through a short Vigreux column at 0.1 mm to yield 1.3 g of impure product (5) boiling at 65°–85° C. [ca. 70% (5) plus ca. 30% of a more polar contaminant by tlc analysis] and 6.7 g of a reasonably pure (5) (bp 85°–110°); tlc (CHCl$_3$) R$_f$0.18; tlc (ether) R$_f$0.64; ir (film) 810, 870, 905, 990, 1030, 1075, 1120, 2870 and 2930 cm$^{-1}$; nmr (CDCl$_3$) δ 1.2–2.3 (14H, m), 3.3–4.2 (8H, m), 4.6–5.3 (3H, m) and 5.5–6.3 ppm (1H, m).

EXAMPLE IV

Preparation of 3-Oxa-1-(tetrahydropyran-2-yloxy)decan-9-ol (6)

A solution of 7.25 g (22.7 mmol) of mercuric acetate was prepared in 20 ml of water by slight warming. This solution was cooled and 40 ml of tetrahydrofuran (THF) was added resulting in the formation of a dispersion of a fine yellow solid. A solution of 5.6 g (23.1 mmol) of (5) in 5 ml of THF was added dropwise to the stirred yellow dispersion. The yellow solid completely dissolved to give a clear colorless solution after about ⅔ of the 5 ml had been added. An extra 3 g of mercuric acetate was dissolved in 10 ml of H$_2$O and then mixed with 20 ml of THF. The resultant additional yellow dispersion was added to the stirred reaction mixture, whereupon a solution of 1 g of sodium borohydride in 20 ml of 3 M aqueous sodium hydroxide was added dropwise to the reaction mixture resulting in an immediate dark mercury precipitate. The resultant mixture was stirred for 0.5 hour whereupon the reaction was quenched by the addition of water, the mercury was allowed to settle and the supernatant decanted and then extracted with ether three times. At this point the combined extract was washed with brine, dried (MgSO$_4$), and evaporated in vacuo to yield the desired product (6). This material showed a major spot on tlc (ether) analysis at R$_f$0.36 for (6) and a minor spot at R$_f$0.69 for some starting material (5). This material was used as is in subsequent reactions.

A small portion of such crude product from a similar later preparation was purified by chromatography on silica gel using a hexane/ethyl acetate elution to yield pure 6; tlc (ether) R$_f$ 0.36; ir (CHCl$_3$) 800, 865, 985, 1030, 1070, 1120, 1240, 1370, 1380, 1460, 2870, 3940 and 3200–3600 cm$^{-1}$; nmr (CDCl$_3$) δ 1.2 (3H, d, J=6.0 Hz), 1.2–2.3 (15H, m), 3.3–4.3 (9H, m) and 4.7 ppm (1H, broad s).

EXAMPLE V

Preparation of 3-oxa-1-(tetrahydropyran-2-yloxy)decan-9-one (7)

Jones reagent was prepared by dissolving 26.7 g of chromic trioxide in 23 ml of concentrated sulfuric acid and diluting this solution with water to 100 ml.

A solution of 24.6 g (94.5 mmol) of (6) in 375 ml of acetone was stirred with cooling in a bath at −15° to −20° C. as 50 ml of the above Jones reagent was added dropwise over 20 minutes. After stirring for an additional 20 min. at −15° C. the reaction was quenched by the dropwise addition of 50 ml of isopropanol. After another 20 min. the reaction mass was mixed with 500 ml water and extracted three times with ether. The combined extracts were washed with brine and then saturated aqueous sodium bicarbonate, dried (MgSO$_4$) and evaporated in vacuo to yield 20.6 g of the desired product (7). This material which showed product at R$_f$0.44 and contaminants at 0.61 and 0.54 was used without purification in the next step. At a later date material prepared in a similar way was purified by chromatography on silica gel using ethyl acetate-hexane (1:3) elution. The use of purified material in the subsequent step did not substantially change yields; tlc (ether) R$_f$0.48; ir (CHCl$_3$) 1020, 1060, 1110, 1700, 2850 and 2920 cm$^{-1}$; nmr (CDCl$_3$) δ 1.0–2.2 (12H, m), 2.17 (3H, s), 2.5 (2H, m), 3.3–4.3 (8H, m) and 4.73 ppm (1H, broad s).

EXAMPLE VI

Preparation of 2-[5-oxa-7-(tetrahydropyran-2-yloxy)heptyl]cyclopentan-1,3,4-trione (8) and 2-(5-oxa-7-hydroxyheptyl)cyclopentan-1,3,4-trione (9)

Ethanol was dried by distillation from sodium ethoxide and a 0.502 g (21.8 mmol) portion of sodium was dissolved in 10 ml of dry ethanol under argon. This solution was then stirred with ice bath cooling as a solution of 2.60 g (10.1 mmol) of (7) in 2.3 ml (21.0 mmol) of diethyl oxalate was added dropwise over 5 min. The resultant solution was then stirred for 1 hour without cooling to give a light red solution and finally refluxed for 1 hour to give a deep red solution. This solution was cooled and 25 ml of 1 N aqueous sodium bicarbonate was added whereupon the resultant mixture was heated under argon at 60°–70° C. for 2.5 hours. The resultant mixture was cooled, diluted with water, acidified with 10% HCl and extracted three times with ethyl acetate. The combined extracts were washed with brine, dried (MgSO$_4$) and evaporated in vacuo to yield 3.5 g of crude (8). This material was chromatographed on silica gel using a gradient elution from pure benzene to pure ethyl acetate. It was found that all of the tetrahydropyranyloxy group was lost during this chromatography and the material isolated was 0.602 g of (9) rather than (8).

Method B

The first stage of the reaction was run in the same manner as above using 25.3 g of (7), 20 ml of diethyloxylate and 4.19 g of sodium in 80 ml of dry ethanol. After one hour of reflux the deep red solution was mixed with 100 ml of 10% aqueous hydrochloric acid and then refluxed for 3 hours. The resultant mixture was saturated with the addition of sodium chloride and then extracted several times with ethyl acetate. This extract was washed with brine, dried (MgSO$_4$) and evaporated in vacuo to yield crude hydrolyzed product (9). This product was purified by chromatography on silica gel with ethyl acetate elution to yield ca. 3.7 g of purified (9) and some mixed fractions of impure (9).

Purified (9) thus obtained can be recrystallized from ethyl acetate-hexane to give very pure (9); tlc (system II) R$_f$0.08 [R$_f$8, 0.23]; ir (KBr) 880, 1060, 1125, 1395, 1675, 1740, 2500–2900 and 3300–3600 cm$^{-1}$; nmr (acetone-d$_6$) δ 1.0–1.8 (4H, m), 2.2–2.6 (2H, m), 2.9 (2H, s), 3.2–3.8 (6H, m) and 5.8 ppm (2H, very broad s); λmax (CH$_3$OH) 324 nm (ε1.07×10$^4$), 232 nm (ε9.8×10$^3$).

EXAMPLE VII

Preparation of 2-(5-oxa-7-hydroxyheptyl)-4RS-hydroxycyclopentan-1,3-dione (10)

A solution of 3.5 g of (9) in 100 ml of isopropanol was hydrogenated over 300 mg of 5% Pd on carbon at 50 PSI hydrogen. After 6 hours very little hydrogen uptake was noted, so an additional 300 mg of 5% Pd on carbon was added, and hydrogenation was continued for 16 hours at 50 PSI. The resultant mixture was filtered through Celite and the filter pad was rinsed with isopropanol. The resultant combined filtrate and rinse were evaporated in vacuo to yield 3.6 gm of (10) which was pure enough to use in the subsequent reaction. A small portion of (10) was purified by column chromatography on silicic acid/Celite (80:20) using gradient elution from ethyl acetate to ethyl acetate containing 10% methanol; tlc (system II) R$_f$ 0.07; ir (film) 880, 1060, 1110, 1270, 1400, 1620 and 2400–3600 cm$^{-1}$; nmr (acetone-d$_6$) δ 1.0–3.0 (8H, complex m), 3.3–3.8 (6H, m), 4.6 (1H, m) and 5.7 (3H, broad s); λmax (CH$_3$OH) 273 nm (ε2.01×10$^4$).

EXAMPLE VIII

Preparation of 2-(5-oxa-7-hydroxyheptyl)-4RS-hydroxycyclopent-2-en-1-one (11)

A solution of 3.0 g (13.0 mmol) of (10) in 25 ml of dry THF was stirred with ice bath cooling under argon as 3.8 ml of triethylamine was added followed by 3.14 g (14.3 mmol) of mesitylenesulfonyl chloride dissolved in 15 ml of dry THF added dropwise over 10 minutes. The resultant mixture was stirred for 0.5 hour with cooling and then 0.5 hour without cooling. The resultant dispersion was transferred to an addition funnel and added dropwise over 15 minutes to a stirred solution of 15 g of sodium bis(2-methoxyethoxy)aluminum hydride (70% in benzene; sold under the trade name Red-al by the Aldrich Chemical Co.) in 25 ml of dry THF with −78° bath cooling under argon. The resultant solution was stirred for 1 hour at −78° and then 0.5 hour at −10° C. At this point a 5 ml portion of methanol was used to quench the reaction slowly at −10°. The reaction product was then mixed with 100 ml of ether, and 100 ml of 10% hydrochloric acid was added dropwise. Solid sodium chloride was added to saturate the aqueous layer which was then extracted first with ether and then with ethyl acetate. Each extract was washed with saturated aqueous sodium bicarbonate. Tlc (system II) analysis of the extracts showed considerable product in the ether extract, but little in the ethyl acetate extract. The extracts were combined, dried (MgSO$_4$) and evaporated in vacuo at which point the residue was dissolved in 50 ml of chloroform-ethanol (90:10) and stirred overnight with 2.5 g of sodium oxalate and 1.0 g of oxalic acid. The resultant mixture was washed with saturated aqueous sodium bicarbonate and the wash solution was back extracted several times with ethyl acetate. The combined extract was dried (MgSO$_4$) and evaporated in vacuo to give a brown oil which was chromatographed on silica gel using benzene to ethyl acetate gradient elution to give 1.0 g of pure (11), tlc R$_f$0.08 (system II); tlc (system II) R$_f$0.08; ir (film) 1060, 1120, 1705, 2870, 2940 and 3200–3600 cm$^{-1}$; nmr (CDCl$_3$) δ 1.0–2.0 (5.2H, m), 2.0–3.2 (5.8H, m), 3.2–4.2 (8.1H, m), 5.0 (1H, m) and 7.3 (1H, broad s); λmax (CH$_3$OH) 222 nm (ε7.9×10$^3$).

EXAMPLE IX

Preparation of 2-[5-oxa-7-(tetrahydropyran-2-yloxy)heptyl]-4RS-(tetrahydropyran-2-yloxy)-cyclopent-2-en-1-one (12)

A solution of 1.0 g (4.67 mmol) of (11) in 10 ml of dry ether was stirred under argon as 1.1 ml (12 mmol) of dihydropyran was added followed by ca. 10 mg of toluenesulfonic acid. After two hours the resultant solution was washed with saturated aqueous NaHCO$_3$. The wash solution was back extracted with ether three times, the combined extracts were dried (MgSO$_4$) and evaporated in vacuo to yield 1.68 g of (12); tlc (ether) R$_f$0.41 ir (film) 810, 865, 980, 1030, 1075, 1120, 1200, 1340, 1715, 2870 and 2940 cm$^{-1}$; nmr (CDCl$_3$) δ 1.2–2.7 (20H, m), 3.3–4.3 (10H, m), 4.6–5.1 (3H, m) and 7.32 (1H, broad s).

The product prepared in this example, i.e., 2-[5-oxa-7-(tetrahydropyran-2-yloxy)heptyl]-4RS-(tetrahydropyran-2-yloxy)cyclopent-2-en-1-one is used in the synthesis of the 3-oxa, 1-carbinol prostaglandins of this invention.

Following Examples X–XVI describe the preparation of the lithium cuprate intermediate which is reacted with intermediate (12) to form the prostaglandin.

EXAMPLE X

Preparation of 2,2-dimethylhexanoic acid (22A, R=n-butyl)

A solution of 102 g (1.02 mol) of diisopropylamine (distilled from calcium hydride) in 730 ml of dry THF was stirred under argon in an ice-bath as a full bottle (1.0 mol) of a solution of n-butyllithium in hexane (Alpha, 2.4 M, ca. 417 ml) was added dropwise at a rate such that the temperature of the reaction mixture held below 8° C. About halfway through the addition the ice-bath was replaced by an ice-methanol bath to better control the temperature at 0° throughout the rest of the addition. The resultant mixture was kept in the cold bath and stirred for 15 minutes before a 41.6 g (0.427 mol) portion of isobutyric acid (21) was added dropwise, again keeping the temperature below 0°. Final portions of the acid were rinsed into the reaction mixture with several ml of dry THF. After another 15 minutes a 57 ml (0.499 mol) portion of 1-iodo-butane was added dropwise. After this addition was complete the ice-bath was used again as the resultant mixture was quenched by the dropwise addition of a solution of 200 ml of concentrated hydrochloric acid in 650 ml of water. The phases were separated and the aqueous phase was back extracted with ether whereupon the combined extract was washed with aqueous sodium bisulfite, dried (MgSO$_4$) and evaporated in vacuo. The residue was distilled at 20 mm to yield 57.8 g of (22A) as an oil, bp 110°–113°; nmr (CDCl$_3$) δ 0.90 (3H, broad t, J=5.7 Hz), 1.18 (6H, s) and 1.0–2.0 ppm (6H - m).

EXAMPLE XI

Preparation of 3,3-dimethyl-2-heptanone (23A, R=n-butyl)

A solution of 14.4 g (100 mmol) of (22A) in 100 ml of dry ether was stirred at 0° C. under argon as 130 ml (237 mmol) of a solution of methyllithium (1.82 M) in ether was added dropwise. The resultant mixture was stirred with ice-bath cooling for 1 hour and then without cooling overnight. The solution was then poured quickly into a vigorously stirred 500 ml portion of water in a large beaker whereupon the phases were separated and the aqueous phase was back extracted twice with ether. The combined extract was dried (MgSO$_4$) and evaporated in vacuo. The residue was distilled at 20 mm to yield 12.7 g of (23A) as a colorless oil, bp 125°–130°; R$_f$ (CHCl$_3$) 0.54; nmr (CDCl$_3$) δ 0.9 (3H, broad t, J=6.0 Hz), 1.12 (6H, s), 1.0–1.8 (6H, m) and 2.14 ppm (3H, s); ir (film) 1130, 1350, 1470, 1705, 2870, 2930 and 2960 cm$^{-1}$.

EXAMPLE XII

Preparation of 4,4-dimethyl-1-hydroxyoct-1-en-3-one (24A, R=n-butyl)

Sodium hydride (9.9 g of 57% oil dispersion) was rinsed twice with dry hexane and then dried by evaporation in vacuo. Argon was used to release the vacuum. Ether (140 ml) followed by 40 ml of methylformate was added to the flask containing the sodium hydride and the resultant mixture stirred under argon as a solution of 22.3 g (157 mmol) of (23) in 35 ml ether was added dropwise. After approximately one-fourth of the solution had been added it was noted that no significant gas evolution was taking place. A 3 ml portion of methanol was added dropwise before the remainder of (23) was added. Shortly after the addition was complete another portion of dry ether (50 ml) was added to the reaction mixture to facilitate stirring. After 3.5 hours the reaction mixture was quenched by the addition of water whereupon the phases were mixed thoroughly and then separated. The ether phase was extracted twice more with water and then three times with 1 N aqueous sodium hydroxide. The water and basic extract were each made acidic with the addition of concentrated hydrochloric acid and then extracted several times with ether at which point the ether extracts were dried (MgSO$_4$) and evaporated in vacuo. The yield from the acidified water phases was 5.0 g and from the acidified basic extracts was 13.8 g of (24A).

This product was not further purified for the next reaction; R$_f$ (CHCl$_3$) 0.46; nmr (CDCl$_3$) δ 0.9 (3H, broad t, J=6.0 Hz), 1.11 and 1.12 (3H each, singlets), 1.0–1.9 (6H, m), 5.75 (1H, d, J=4.7 Hz), 7.5 (1H, broad s) and 8.14 ppm (1H, broadened d, J=4.7 Hz); ir (film) 1590, 1685, 1700, 2870, 2930, 2960 and 3100–3600 cm$^{-1}$ (broad).

EXAMPLE XIII

Preparation of 4,4-dimethyl-1-toluenesulfonyloxyocta-1-en-3-one (25A)

Unpurified (24A) (18.8 g, 111 mmol) was dissolved in 190 ml of dry ether. This solution was stirred with ice-bath cooling under argon as first 22 ml (158 mmol) of triethylamine was added in one portion followed by a solution of 24.3 g (128 mmol) of toluenesulfonyl chloride in 100 ml of dry ether added dropwise over 15 minutes. The resultant mixture was stirred with ice-bath cooling for 1.5 hours whereupon methanol (4 ml) was added to the reaction mixture to quench excess toluenesulfonyl chloride. The resultant mixture was stirred another 8 minutes before it was washed sequentially with 10% aqueous hydrochloric acid, brine and then saturated aqueous sodium bicarbonate. The resultant solution was dried (MgSO$_4$) and then evaporated in vacuo to yield 40 g of a residue containing (25A), i.e.,

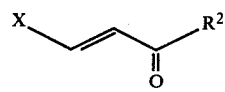

where R$^2$ is 1,1-dimethylpentyl and X is p-toluenesulfonyloxy. This residue was used without purification for the subsequent reaction. R$_f$ (CHCl$_3$) 0.23 and 0.39 (cis and trans isomers); nmr (CDCl$_3$) δ 0.86 (3H, broad t, J=6.0 Hz), 1.05 (6H, s), 1.0–1.8 (6H, m), 2.48 (3H, s), 6.41 (1H, d, J=11.8 Hz), 7.48 (2H, d, J=8.5 Hz), 7.72 (1H, d, J=11.8 Hz) and 7.93 ppm (2H, d, J=8.5 Hz).

EXAMPLE XIV

Preparation of 4,4-dimethyl-1-iodoocta-1E-en-3-one (27A)

The sample of (25A) was dissolved in 250 ml of dry acetone and stirred overnight under argon with 25.2 g of sodium iodide and 1.0 g of lithium iodide. The (CHCl$_3$) analysis the next day of the reaction mixture showed little or no reaction had taken place. A 0.25 ml portion of concentrated sulfuric acid was added to the dark colored reaction mixture and it was then heated to reflux using an oil bath. The mixture rapidly became very viscous and the analysis after a few minutes showed considerable amounts of (27A) had formed at the expense of (25A). After 1 hour of reflux the resultant very dark colored reaction mixture was evaporated in vacuo. The residue was mixed with ether and washed with aqueous sodium thiosulfate and then with saturated aqueous sodium bicarbonate. The resultant extract was dried (MgSO$_4$) and evaporated in vacuo. The resultant 27.8 g of residue was distilled in vacuo to yield 18.7 g of (27A) as a yellow oil, bp 78°–88° (0.2 mm); R$_f$ (CHCl$_3$) 0.58; nmr (CDCl$_3$) δ 0.90 (3H, broad t, J=6.0 Hz), 1.14 (6H, s), 1.0–1.8 (6H, m) 7.66 (1H, d, J=14.8 Hz) and 8.07 ppm (1H, d, J=14.8 Hz); ir (film) 940, 1040, 1080, 1470, 1560, 1688, 2860, 2930 and 2960 cm$^{-1}$.

EXAMPLE XV

Preparation of 4,4-dimethyl-3RS-hydroxy-1-iodooct-1-E-ene (28A)

A solution of 3.7 g of (27A) in 100 ml of absolute ethanol was stirred under argon with ice-bath cooling as 1.5 g of sodium borohydride was added. The resultant mixture was stirred with cooling for 15 minutes whereupon the reaction mixture was quenched by the addition of water and then evaporated in vacuo. The residue was mixed with ether and washed with water at which point the aqueous wash solution was back extracted with ether. The combined extract was dried (MgSO$_4$) and evaporated in vacuo to yield 3.4 g of (28A); R$_f$ (CHCl$_3$) 0.36; nmr (CDCl$_3$) δ 0.9 (9H, m), 1.0–1.7 (6H, m), 1.93 (1H, s), 3,86 (1H, d, J=6.0 Hz), 6.36 (1H, d, J=14.0 Hz) and 6.77 ppm (1H, d of d, J=14.0, 6.0 Hz); ir (film) 950, 1020, 1380, 1470, 1610, 2870, 2930, 2960 and 3100 to 3600 cm$^{-1}$.

EXAMPLE XVI

Preparation of 4,4-dimethyl-3RS-(1-ethoxyethoxy)-1-iodooct-1E-ene (13A)

A solution of 851 mg (3.01 mmol) of (28A) in 3 ml of dry ether was stirred under argon with ice-bath cooling as 0.33 ml (3.45 mmol) of ethylvinyl ether was added followed by ca. 5 mg of toluenesulfonic acid (hydrate). The ice-bath was removed and the reaction mixture stirred without cooling; after 1 hour a tlc (CHCl$_3$) analysis showed considerable product. Another 0.03 ml of ethylvinyl ether was added and after 0.5 hour a tlc analysis showed that the reaction had gone to completion. At this point the resultant reaction mixture was washed with saturated aqueous sodium bicarbonate and the wash solution back-extracted once with ether. The combined extract was dried (Na$_2$SO$_4$) and evaporated to yield 885 mg of (13A) which was used directly in the next reaction; R$_f$(CHCl$_3$) 0.46 and 0.51 (diastereomeric isomer pair); nmr (CDCl$_3$) δ 0.7–1.9 (21H, m), 3.4–3.9 (3H, m), 4.70 (1H, q, J=5.0 Hz), 6.23 (1H, d, J=15 Hz) and 6.57 ppm (1H, d of d, J=15, 7 Hz).

EXAMPLE XVII

Preparation of ±16,16-dimethyl-3-oxa-1,11α,15R and S-trihydroxyprost-13E-en-9-one (TR-4616 and TR-4617)

A solution of 1.04 g (2.94 mmol) of 4,4-dimethyl-3RS-(1-ethoxyethoxy)1-iodooct-1E-ene (13A) in 10 ml of dry ether was stirred under argon with −78° C. bath cooling as 4.08 ml (5.58 mmol) of a 1.44 M solution of t-butyllithium in pentane was added dropwise quickly via syringe. The resultant solution was stirred for 2 hours at −78°. A second solution was prepared at ambient temperature by stirring a mixture of 0.384 g (2.94 mmol) of dry copper (I) pentyne, 1.1 ml of hexamethylphosphoroustriamide and 5 ml of dry ether until they had become homogeneous. This second solution was transferred to the alkyl lithium solution dropwise via syringe as stirring was continued at −78°. After another 15 minutes a solution of 0.566 g (1.48 mmol) of (12) in 4 ml of dry ether was added dropwise. The resultant dispersion was then stirred with −20° C. bath cooling for 3 hours whereupon it was quenched at −20° by the addition of 60 ml of 2% aqueous sulfuric acid. The resultant mixture was shaken thoroughly and then filtered through Celite and the filter pad rinsed thoroughly with ether. The filtrate phases were separated, at which point the ether phase was washed with brine and then with saturated aqueous sodium bicarbonate, dried (MgSO$_4$) and evaporated in vacuo. The residue was stirred under argon with 50 ml of acetic acid-water-THF (65:35:10) for 18 hours. The resultant solution was evaporated in vacuo and the residue mixed with ethyl acetate and washed with saturated aqueous sodium bicarbonate. The washed solution was back-extracted three times with ethyl acetate, the combined extract was dried (MgSO$_4$) and evaporated to yield a mixture of the desired products TR-4616 and TR-4617. This mixture was chromatographed on silicic acid-Celite (80:20) using a benzene to ethyl acetate gradient to yield 94 mg of the less polar 15S material.

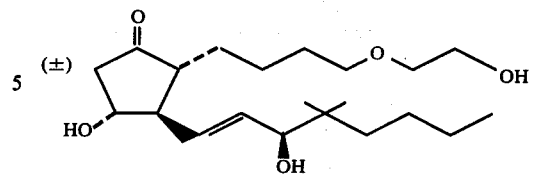

and 143 mg of the more polar 15R material

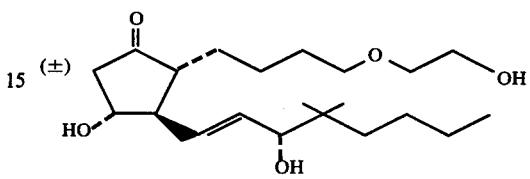

tlc (system II) R$_f$0.16; ir (CHCl$_3$) 880, 970, 1045, 1070, 1110, 1740, 2860, 2930 and 3200–3600 cm$^{-1}$; nmr (CDCl$_3$) δ 0.9 (9H, broad s), 1.0–2.0 (12H, m), 2.0–4.3 (15H, m) and 5.75 ppm (2H, m); ms (70 eV) m/e 352, 334, 308, 271, 253, 218. TR-4617: tlc (system II) R$_f$0.22; ir, nmr and ms much the same as for TR-4616 above.

EXAMPLE XVIII

Preparation of 3-cyclohexyl-1-chloroprop-1E-en-3-one (25C)

Acetylene was passed sequentially through an aluminum oxide trap, two concentrated (98%) sulfuric acid traps and an empty trap. A 2-liter, 3-necked flask was then filled with an atmosphere of the acetylene through one sidearm using a glass tube and adaptor. Carbon tetrachloride (100 ml) was then added to the flask. The flask was cooled by an external ice-water bath, and additional acetylene was bubbled in for several minutes. At this point the central neck of the flask was fitted with a stirrer and the remaining sidearm was fitted with a condensor. The gas addition tube was removed from the reaction flask and 325 g of aluminum chloride was added to the carbon tetrachloride. Acetylene was again bubbled through the reaction mixture. The gas addition tube was then replaced by an addition funnel which contained 300 g of cyclohexanecarboxylic acid chloride (26C) in 130 ml of carbon tetrachloride. That solution was added slowly to the stirred reaction mixture whereupon the addition funnel was replaced by the gas addition tube and acetylene addition was continued for 4 hours while the reaction was stirred and cooled. The reaction mixture then was poured over a mixture of 1000 g of ice and 1100 ml of saturated brine in a large beaker. The phases of the resultant mixture were then separated, and the aqueous phase was extracted three times with ether. Combined organic phases were washed with 10% aqueous hydrochloric acid and then with saturated aqueous sodium bicarbonate. They were dried over anhydrous magnesium sulfate and evaporated in vacuo to yield 103 g (44%) of pure (25C) which had the following spectral properties: nmr (CDCl$_3$) δ 0.9–2.8 (11H, m), 6.7 (1H, d, J=14 Hz) and 7.40 ppm (1H, d, J=14 Hz).

EXAMPLE XIX

Preparation of 3-cyclohexyl-1-iodoprop-1E-en-3-one (27C)

A solution of 153 g of (25C) and 500 g of sodium iodide in 700 ml of dry acetone (distilled from anhydrous potassium carbonate) was refluxed under argon for 18 hours. The solvent was then removed by evaporation in vacuo. The residue was mixed with water and extracted three times with ether. The combined extract was dried over anhydrous magnesium sulfate and then evaporated in vacuo to yield 238 g of the desired product which had the following spectral properties: nmr (CDCl$_3$) δ 0.9–2.8 (11H, m), 7.30 (1H, d, J=15 Hz) and 7.92 ppm (1H, d, J=15 Hz).

EXAMPLE XX

Preparation of 3-cyclohexyl-3RS-hydroxy-1-iodoprop-1E-ene (28C)

A solution of 238 g of (27C) in 2000 ml of absolute ethanol was stirred with cooling (−10° C.) as 120 g of sodium borohydride was slowly added. After addition of the borohydride was completed, the reaction mixture was stirred and solvent was removed by evaporation in vacuo to yield 205 g of the desired product which had the following spectral properties: nmr (CDCl$_3$) δ 0.8–2.4 (11H, m), 3.0 (1H, s), 3.86 (1H, t, J=15 Hz), 6.28 (1H, d, J=14.5 Hz) and 6.67 ppm (1H, d of d, J=14.5, 6.0 Hz); ir (CHCl$_3$) 3600, 3450 (broad), 1600, 1450, 1000 and 953 cm$^{-1}$.

EXAMPLE XXI

Preparation of 3-cyclohexyl-3R-hydroxy-1-iodoprop-1E-ene (29C)

A 16.75 g portion of sodium hydride oil dispersion (57%) was placed in a 2 liter, 3-necked flask under dry nitrogen and was rinsed with pentane. The flask was fitted with a stirrer, condensor and addition funnel. The sodium hydride was dispersed in a solution of 400 ml of anhydrous dimethylformamide and 200 ml of anhydrous benzene and then 58.5 g of phthalic anhydride was added. A solution of 104.8 g of (28C) in 220 ml of anhydrous benzene was added to the reaction mixture from the addition funnel over 30 minutes. The reaction mixture was then heated at 50° to 60° C. for 2 hours, cooled and poured into cold water. A 100 ml portion of 15% aqueous sodium hydroxide was added to the resultant mixture before it was extracted several times with hexane. The hexane extract was dried over anhydrous magnesium sulfate and evaporated in vacuo to yield some recovered starting material. The aqueous phase was acidified with concentrated hydrochloric acid and extracted with ether. The combined extract was washed with saturated aqueous sodium sulfate, dried over anhydrous MgSO$_4$ and then evaporated in vacuo to yield 88.4 g of 3-cyclohexyl-1-iodoprop-1E-en-3RS-yl hemiphthalate which had the following spectral properties: nmr (CDCl$_3$) δ 0.8–2.2 (11H, m), 5.35 (1H, m), 6.65 (2H, m), 7.5–8.3 (4H, m) and 12.2 (1H, s); ir (CHCl$_3$) 3700-2380 (broad), 1720, 1670, 1640, 1600 and 900 cm$^{-1}$.

A 28.6 g portion of (−)-α-methylbenzylamine was slowly added to a solution of 97.6 g of 3-cyclohexyl-1-iodoprop-1E-en-3RS-yl hemiphthalate in 270 ml of methylene chloride. The solvent was removed in vacuo and the residue recrystallized from acetonitrile/methanol to yield 17.4 g of a first crop of crystals (mp 148°–149° C.) and 14.3 g of a second crop of crystals (mp 144°–145° C.). These crystals were in turn recrystallized from acetonitrile to give a total of 18.1 g of the (−)-α-methylbenzylammonium salt of 3-cyclohexyl-1-iodoprop-1E-en-3RS-yl hemiphthalate: mp 151.8°–152.0° C.; [α]$_D$ −19.9° (c 1.03), CH$_3$OH); nmr (CDCl$_3$) 0.8–2.2 (14H, m), 4.30 (1H, m), 5.13 (1H, d of d, J=5.2, 2.0 Hz), 6.45 (2H, m), 7.3–7.7 (9H, m) and 8.37 ppm (3H, m).

A mixture of 21.4 g of the (−)-α-methylbenzylammonium salt of 3-cyclohexyl-1-iodoprop-1E-en-3RS-yl hemiphthalate and 200 ml of 15% aqueous sodium hydroxide was heated with stirring under nitrogen on a steam bath for 2 hours. The resultant mixture was cooled and extracted three times with ethyl acetate and the combined extract washed with 4 M hydrochloric acid twice and then with saturated aqueous sodium sulfate. The extract was then dried over anhydrous magnesium sulfate and evaporated in vacuo to yield 10.5 g of the desired product (29C), bp 107°–115° C. The analytical data for the pure product are as follows: [α]$_D$ +19.2° (c 1.05, CH$_3$); nmr (CDCl$_3$) δ 0.8–2.4 (11H, m), 3.0 (1H, s), 3.86 (1H, t, J=5.5 Hz), 6.28 (1H, d, J=14.5 Hz) and 6.67 ppm (1H, d of d, J=14.6, 6.0 Hz); ir (CHCl$_3$) 3600, 3450 (broad), 1600, 1450, 1000 and 953 cm$^{-1}$.

EXAMPLE XXII

Preparation of 3-cyclohexyl-3R-(1-ethoxyethoxy)-1-iodoprop-1E-ene (13*C)

A solution of 2.8 g of (29C) and 1.4 ml of ethylvinyl ether in 10 ml of dry diethylether was stirred under argon with about 5 mg of toluenesulfonic acid for 2 hours. The resultant solution was washed with saturated aqueous sodium bicarbonate and the aqueous phase extracted with ether whereupon the combined ether phases were dried over anhydrous sodium sulfate and then evaporated in vacuo to yield 3.4 g of 13*C as a faint yellow oil. [α]$_D$ −44.4° (c 1.02, CH$_3$OH); nmr (CDCl$_3$) δ 0.8–2.2 (17H, m), 3.5 (3H, m), 4.7 (1H, m) and 6.0–6.8 ppm (2H, m); ir (CHCl$_3$) 950, 1010, 1050, 1075, 1090, 1120, 1170, 1380, 1450, 1605, 2850, 2930 and 2980 cm$^{-1}$.

EXAMPLE XXIII

Preparation of 16,20-methano-3-oxa-1,11α,15R-trihydroxyprost-13E-en-9-one and 16,20-methano-oxa-1,11β,15R-trihydroxy-8,12-bisisoprost-13E-en-9-one (TR-4856 and TR-4853)

A solution of 1.05 g (3.0 mmol) of 3-cyclohexyl-3R-(1-ethoxyethoxy)-1-iodoprop-1E-ene (29C) in 6 ml of dry ether was stirred under argon with −78° C. bath cooling as 5.44 ml (6.0 mmol) of a 1.10 M solution of t-butyllithium in pentane was added dropwise quickly via syringe. The resultant solution was stirred for 2 hours at −78°. A second solution was prepared at ambient temperature by stirring a mixture of 0.40 g (3.0 mmol) of dry copper (I) pentyne, 1.1 ml of hexamethylphosphoroustriamide and 3 ml of dry ether until they had become homogeneous. This second solution was transferred to the alkyl lithium solution dropwise via syringe as stirring was continued at −78°. After another 15 minutes a solution of 0.76 g (2.0 mmol) of (12) in 4 ml of dry ether was added dropwise. The resultant dispersion was then stirred with −20° C. bath cooling for 2 hours, quenched at −20° by the addition of aqueous 2% H₂SO₄ and then shaken vigorously. The material was then filtered through Celite and the filter pad was rinsed thoroughly with ether. The filtrate phases were separated and the ether phase was washed with brine and then saturated aqueous NaHCO₃ whereupon it was dried (MgSO₄) and evaporated in vacuo. The residue was stirred under argon with 50 ml of acetic acid-water-THF (65:35:10) for 3 days and then evaporated in vacuo. The residue was mixed with ethyl acetate and washed with saturated aqueous NaHCO₃ and the wash solution back-extracted three times with ethyl acetate. The combined extract was dried (MgSO₄) and evaporated in vacuo to yield a mixture of TR-4856 and TR-4853. This residue was chromatographed on silicic acid-Celite (80:20) using benzene to ethyl acetate gradient elution to yield semi-pure materials which were rechromatographed on silica gel using ethyl acetate elution to yield 30 mg of the less polar 8,12-bisiso material TR-4853:

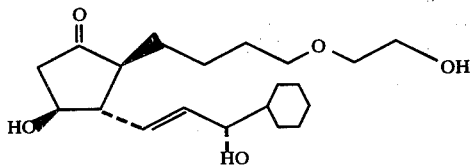

and 50 mg of the more polar material TR-4856:

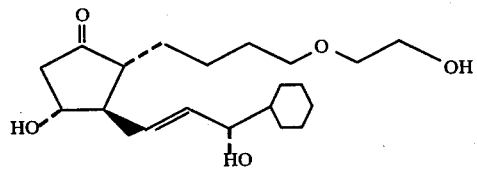

tlc (system II) R$_f$ 0.15; [α]$_D$ −42.8° (c 1.0, CHCl₃); ir (CHCl₃) 885, 970, 1075, 1120, 1240, 1450, 1740, 2860, 2930 and 3200–3600 cm⁻¹; nmr (CDCl₃) δ 0.8–2.8 (24H, m), 2.8–4.2 (8H, m) and 5.65 ppm (2H, m); ms (70 eV) m/e 336, 318, 292, 274, 271, 253, 235, 230, 209, 191. TR-4853: tlc (system II) R$_f$ 0.18; [α]$_D$ +58.0° (c 1.0, CHCl₃); ir, nmr and ms much the same as for TR-4856 above.

EXAMPLE XXIV

Preparation of 3S-(1-tetrahydropyran-2-yloxy)-1-iodooct-1E-ene (13*B)

A solution of 7.5 g (29.5 mmol) of 3S-hydroxy-1-iodooct-1E-ene [(29B) prepared as described by E. J. Corey and W. J. Beames, J. Amer. Chem. Soc., 94, 2710 (1972)] in 50 ml of dry ether was stirred at 0° C. under argon as 3.7 ml (41 mmol) of freshly distilled commercial dihydropyran was added followed by 10 mg of p-toluenesulfonic acid. The resultant mixture was stirred with ice bath cooling for 0.5 hour and then left at 0°–5° C. overnight (16 hours). The resultant solution was washed with saturated aqueous sodium bicarbonate and the wash solution back-extracted with ether, the combined extract dried (Na₂SO₄) and evaporated in vacuo. Benzene was added and then removed by evaporation in vacuo to remove traces of water. The yield was 9.7 g of pure (13*B); tlc (CHCl₃) R$_f$ 0.45; ir (film) 940, 1020, 1050, 1080, 1120, 2850 and 2930 cm⁻¹; nmr (CDCl₃) δ 0.90 (3H, broad t, J=6.0 Hz), 1.0–2.2 (14H, m), 3.3–4.3 (3H, m), 4.7 (1H, broad s) and 6.2–7.0 ppm (2H, complex m).

EXAMPLE XXV

Preparation of 3-oxa-1,11α,15S-trihydroxyprost-13E-en-9-one and 3-oxa-1,11β,15S-trihydroxy-8,12-bisisoprost-13E-en-9-one (TR-4650 and TR-4649)

A solution of 1.02 g (3.00 mmol) of 3S-(tetrahydropyran-2-yloxy)-1-iodooct-1E-ene in 10 ml of dry ether was stirred under argon with −78° C. bath cooling as 4.17 ml (6.00 mmol) of a 1.44 M solution of t-butyllithium in pentane was added dropwise quickly via syringe. A second solution was prepared at ambient temperature by stirring a mixture of 0.392 g (3.00 mmol) of dry copper (I) pentyne, 1.1 ml of hexamethylphosphoroustriamide and 5 ml of dry ether until they had become homogeneous. This second solution was transferred to the alkyl lithium solution dropwise via syringe as stirring was continued at −78° C. After another 15 minutes a solution of 0.564 g (1.47 mmol) of (12) in 4 ml of dry ether was added dropwise. The resultant dispersion was then stirred with −20° bath cooling for 2 hours. It was quenched at −20° by the addition of 70 ml of 2% aqueous sulfuric acid and the resultant mixture shaken thoroughly and then filtered through Celite. The filter pad was rinsed thoroughly with ether whereupon the combined filtrate phases were washed with brine and then saturated aqueous sodium bicarbonate, dried (MgSO₄) and evaporated in vacuo. The residue was stirred with 50 ml of acetic acid-water-THF (65:35:10) under argon for 3 days at room temperature, the solvent removed by evaporation in vacuo and the residue mixed with ethyl acetate and washed with saturated aqueous NaHCO₃. At this point the wash solution was back-extracted three times with ethyl acetate, the combined extract dried (MgSO₄) and evaporated in vacuo to yield a mixture of TR-4650 and TR-5649. This material was chromatographed on silicic acid/Celite (80:20) using a benzene to ethyl acetate gradient to yield 32 mg of the less polar 8,12-bisiso material TR-4649:

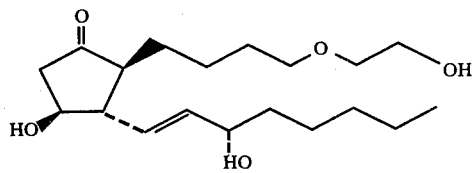

and 65 mg of the more polar material TR-4650:

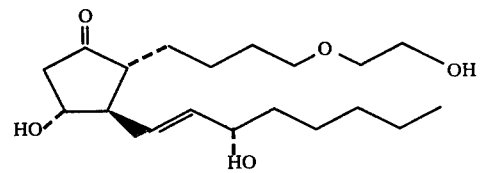

TR-4650: tlc (system II) R$_f$ 0.15; [α]$_D$ −67.8° (c 1.0, CHCl₃); ir (CHCl₃) 880, 965, 1060, 1110, 1230, 1355, 1450, 1730, 2860, 2920 and 3200–3600 cm⁻¹; nmr (CDCl₃) 0.90 (3H, broad t, J=6.0 Hz), 1.0–2.0 (14H, m), 2.0–3.2 (7H, m), 3.2–4.5 (8H, m) and 5.72 ppm (2H, m); ms (70 eV) m/e 324, 306, 280, 271, 253, 218. TR-4649:

tlc (system II) $R_f 0.18$; $[\alpha]_D + 64.5°$ (c 1.0, $CHCl_3$); ir, nmr and ms much the same as for TR-4650 above.

EXAMPLE XXVI

The various utilities of the novel prostaglandins disclosed herein were determined as follows:

Inhibition of Platelet Aggregation by Prostaglandins In Vitro

The ability of test compounds to inhibit platelet aggregation is determined by a modification of the turbidometric technique of Born (1962). Blood is collected from human volunteers, who have not ingested aspirin or aspirin-containing products within the last two weeks, in heparinized Vacutainers (Becton, Dickinson and Co.) and is allowed to settle for one hour. The platelet rich plasma (PRP) supernates are collected and pooled. Siliconized glassware is used throughout.

In a representative assay, 1.9 ml of PRP and 0.2 ml of test compound at the appropriate concentrations (0.001 to 100 mcgm), or 0.2 ml of distilled water (control procedure) are placed in sample cuvettes. The cuvettes are placed in a 37° incubation block for 15 minutes, and then a Coleman Jr. Spectrophotometer (Model 6C) linked to a strip chart recorder. After 30-60 seconds, 0.2 ml of a solution, prepared by diluting a claf-skin collagen solution (Worthington Biochemical) 1:9 with Tyrodes Solution, is added to each cuvette. Platelet aggregation is evidenced by a decrease in optical density.

Calculation of the degree of inhibition of platelet aggregation, exhibited by each concentration of test compound, is accomplished according to the method of Caprino et al (1973). An $IC_{50}$ value* is then determined graphically and a value judgement is assigned as follows:

| Response | Value Judgement |
|---|---|
| $IC_{50} < 0.001$ mcgm | +5 |
| $IC_{50} > 0.001$ mcgm and $< 0.01$ mcgm | +4 |
| $IC_{50} > 0.01$ mcgm and $< 0.1$ mcgm | +3 |
| $IC_{50} > 0.1$ mcgm and $< 1.0$ mcgm | +2 |
| $IC_{50} > 1.0$ mcgm | +1 |
| Compound exhibits no inhibitory (+) or stimulatory (−) activity | 0 |
| Produces <25% increase in aggregation at highest dosage tested | −0 |
| Produces >25% and <50% increase in aggregation at highest dosage tested | −1 |
| Produces >50% and <75% increase in aggregation in highest dosage tested | −2 |
| Produces >75% and <100% increase in aggregation at highest dosage tested | −3 |
| Produces >100% increase in aggregation at highest dosage tested | −4 |

*$IC_{50}$ is the concentration of compound which produces 50% inhibition of the response measured in the absence of the compound.

References: Born, G. V. R., Nature 194, 927 (1962); Caprino, L., Boreli, F. and Falchetti, R., Arzneim-Forsch, 23, 1277 (1973).

Evaluation of the Effects of Prostaglandin Analogs on the Guinea Pig Trachea In Vitro A male guinea pig weighing 200-500 gm is killed by a blow on the head. A 20 mm length of the trachea is dissected from the animal, transferred to a petri dish containing Kreb's solution aerated with 95% $O_2$ and 5% $CO_2$ at 37° and cut longitudinally opposite the tracheal muscle. The tissue is then cut transversely three quarters of the distance across the tissue and this procedure is continued for the whole tissue. The ends of the trachea can be pulled to form a zig-zag shaped strip. The tracheal strip used in the experiment is approximately 30 mm when extended under 0.25-0.5 gm load in the tissue bath. Cotton thread is tied to one end of the tissue, and linen thread to the other. It is attached via the linen thread to a glass hook in a 5 ml isolated tissue bath containing Kreb's solution at 37° and aerated with a mixture of 95% $O_2$ and 5% $CO_2$. The opposite end is attached via cotton to an isotonic Harvard transducer (Model 386 Heart/Smooth Muscle Transducer, Harvard Apparatus). The load on the transducer level is small, usually 0.3 gm, with a range of 0.25-0.5 gm and the magnification high, 80-fold using an appropriate twin-channel pen recorder. A minimum of thirty minutes is allowed before applying a drug to the tissue. Drugs are then applied (in volumes of 0.5 ml) at thirty minute intervals, being in contact with the tissue for five minutes followed by an overflow washout time of twenty seconds.

Prostaglandin $E_1$, at a bath concentration of 0.1 mcg/ml, is then tested repeatedly on two such strips, obtained from two different animals, until two responses (the values of which are recorded) differing by no more than 25% occur. This concentration of $PGE_1$ should elicit a relaxation expressed as from 10 to 30 mm of recorder pen excursion. A test compound is then added to the same two strips at bath concentrations of 0.01, 0.1, 1.0 and 10.0 mcg/ml and the effects of the compound are recorded. After the test compound has been evaluated at the highest concentration, $PGE_1$ is retested at 0.1 mcg/ml (and the value of the response recorded) to insure that the viability of the strips was retained during the experiment. The mean of the effects of the test compound on the two strips is then calculated for each concentration, and, based on the resulting values, a value judgement is assigned as follows:

| Response | Value Judgement |
|---|---|
| More relaxation at 0.01 mcg/ml than that elicited by $PGE_1$ | R4 |
| More relaxation at 0.1 mcg/ml than that elicited by $PGE_1$ | R3 |
| More relaxation at 1.0 mgc/ml than that elicited by $PGE_1$ | R2 |
| More relaxation at 10.0 mcg/ml than that elicited by $PGE_1$ | R1 |
| More than 0 but less relaxation at any concentration than that elicited by $PGE_1$ | R0 |
| No effect at any concentration | 0 |
| More than 0 but less contraction at any concentration than the degree of relaxation elicited by $PGE_1$ | C0 |
| More contraction at 10.0 mcg/ml than the degree of relaxation elicited by $PGE_1$ | C1 |
| More contraction at 1.0 mcg/ml than the degree of relaxation elicited by $PGE_1$ | C2 |
| More contraction at 0.1 mcg/ml than the degree of relaxation elicited by $PGE_1$ | C3 |
| More contraction at 0.01 mcg/ml than the de- | C4 |

| Response | Value Judgement |
|---|---|
| gree of relaxation elicited by $PGE_1$ | |

[1] If less than 10 mm relaxation is observed, retest $PGE_1$ at 1.0 mcg/ml; if less than 10 mm relaxation is seen at this concentration prepare new tracheal strips. If more than 30 mm relaxation is observed at 0.1 mcg/ml $PGE_1$, retest $PGE_1$ at a concentration of 0.01 mcg/ml; if more than 30 mm relaxation is observed at this concentration also, retest $PGE_1$ at 0.001 mcg/ml. If it is necessary to use a concentration of $PGE_1$ other than 0.1 mcg/ml in order to obtain the desired response (i.e., 10 to 30 mm relaxation), adjust the listed concentrations of the test compound up one or down one or two orders of magnitude as appropriate.

Evaluation of the Effects of Prostaglandin Analogues on Gastric Secretion of the Rat A procedure based on that described by Lipmann (1969) is used to assess the influence of test compound on gastric secretion. Rats of one sex weighing 150 to 200 gm are randomly divided into groups of six animals each and fasted for 48 hours previous to the experiments, water being available ad libitum. The animals are anesthetized with ether, the abdomen opened through a midline incision, and the pylorus ligated. Test compounds are diluted from stock solution so as to administer a dose of 1.5 mg/kg in a volume equivalent to 1 ml/kg. Subcutaneous injections are applied immediately after surgery and again 2 hours later, so that a total dose of 3.0 mg/kg is administered. Dilutions are made with phosphate buffer (pH 7.38) as recommended by Lee et al (1973), in order to insure adequate stability of drugs at the subcutaneous depot. Each compound is tested in one group of rats; an additional control group received only one vehicle.

Four hours after pyloric ligation the animals are killed with ether, the cardias ligated and the stomachs removed. The volume of gastric secretion is measured and the contents centrifuged at 5000 rpm for 10 minutes. Total acid in the supernatant is titrated against a 0.1 N sodium hydroxide solution and the amount expressed in mEq.

Volume and total acid values of the treated group are compared with those of the controls by the test. Antisecretory activity is scored according to the following scale:

| % Decrease in Acidity | Value Judgement |
|---|---|
| <26 | 0 |
| 26–50, not significant | 1 |
| 26–50, significant | 2 |
| 51–75 | 3 |
| 76–100 | 4 |

References:
Lee, Y. H., Cheng, W. O., Bianchi, R. G., Mollison, K. and Hansen, J., Prostaglandins 3: 29 (1973); and Lipmann, W., J. Pharm. Pharmacol. 21: 335 (1968).

Evaluation of the Effects of Prostaglandin Analogues on Blood Pressure in the Hypertensive Rat The acute antihypertensive activity of test compounds is determined in rats made hypertensive by the procedure of Grollman (1944). Female rats weighing between 60 and 100 g are anesthetized with ether, the right kidney approached through a flank retroperitoneal incision, decapsulated and tied with a figure-of-eight ligature. The animals are left to recover and two weeks later are again anesthetized and the contralateral kidney removed. Four weeks after the second operation the rats are subjected to indirect blood pressure measurements and those showing systolic pressure values greater than 160 mmHg are selected for drug testing.

Blood pressure is measured in the tail with an inflatable occluding cuff placed at the base of the extremity and a pulse detector located distally. The cuff is inflated to approximately 300 mmHg and is slowly deflated until pulsations appear, indicating the level of systolic pressure; diastolic pressure is not recorded by this procedure. All measurements are carried out in unanesthetized, unsedated animals maintained in a warm environment during the recording procedure and for at least 6 hours before. In all cases, three pressure readings are obtained in succession and mean values are calculated thereof.

Experiments are carried out in groups of five hypertensive rats in which systolic pressure is determined immediately before and 2, 4, 6 and 8 hours after the intraperitoneal administration of the test compound at a dose of 1 mc/kg. Drugs are diluted from stock solutions with phosphate buffer (Lee et al, 1973), so as to inject this quantity in a volume of 1 ml/kg. Changes from control blood pressure values are calculated for each interval both in mmHg and in percent and evaluated for significance by means of Wilcoxon's signed rank test (Wilcoxon and Wilcox, 1964). Activity of the compound is scored as follows:

| Blood Pressure Decrease | Value Judgement |
|---|---|
| Not significant at any time interval | 0 |
| Significant at one time interval | 1 |
| Significant at two time intervals | 2 |
| Significant at three time intervals | 3 |
| Significant at all four time intervals | 4 |

References: Grollman, A., Proc. Soc. Exper. Biol. Med., 57:102 (1944); Lee, Y. H., Cheng, W. O., Bianchi, R. G., Mollison, K. and Hansen, J., Prostaglandins 3:29 (1973); Wilcoxon, F. and Wilcox, R. A., Some Rapid Approximate Statistical Procedures, Lederle Laboratories, Pearl River (1964).

The foregoing screening techniques were used to test the prostaglandins of the instant invention. The results of these tests are set out in Table I:

TABLE I

Summary of Activity of Prostaglandin Analogues

| Analogue | Ex. | Guinea Pig Trachea | Blood Pressure Hypertensive Rat | Gastric Secretion | Platelet Aggregation |
|---|---|---|---|---|---|
| TR-4616 | XVII | C0 | 0 | 2 | 1 |
| TR-4617 | XVII | C1 | 1 | 0 | 1 |
| TR-4649 | XXV | C0 | NT | 0 | 0 |
| TR-4650 | XXV | C0 | 1 | 0 | 1 |
| TR-4853 | XXIII | C0 | NT | 0 | 1 |
| TR-4856 | XXIII | R0 | 2 | 0 | 1 |

NT = Not Tested

Referring to Table I, it can be determined that compounds active in the platelet aggregation assay as inhibitors would be expected to be useful as potential antithrombotic agents.

Compounds active in the guinea-pig trachea assay as relaxants are useful as potential bronchodilators and hence would be of value as anti-asthmatic agents. Those compounds which have been observed to cause constriction of the guinea pig trachea are potentially useful as rat poisons.

Compounds which inhibit gastric acid secretion, e.g., TR-4616 would be expected to have utility in the treatment of gastric hyperacidity and so aid the healing of peptic ulcers. Compounds having activity in the hypertensive rat screen would have potential utility as antihypertensive agents.

What is claimed is:

1. 3-oxa carbinol analogs of prostaglandin $E_1$ having the structural formula:

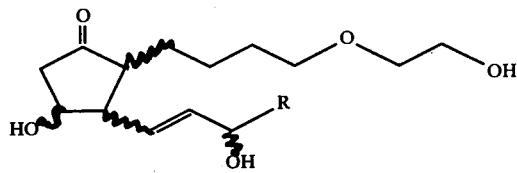

wherein R is n-alkyl of 4 to 6 carbon atoms, cycloalkyl of 5 to 7 carbon atoms or 1,1-dimethylalkyl of 6 to 8 carbon atoms.

2. A compound as defined in claim 1 wherein R is n-alkyl of 4 to 6 carbon atoms.

3. A compound as defined by claim 2 wherein R is pentyl.

4. 3-oxa-1,11α,15S-trihydroxyprost-13E-en-9-one.

5. 3-oxa-1,11β,15S-trihydroxy-8,12-bisisoprost-13E-en-9-one.

6. A compound as defined by claim 1 wherein R is 1,1-dimethylalkyl of 6 to 8 carbon atoms.

7. ±16,16-dimethyl-3-oxa-1,11α,15R-trihydroxyprost-13-E-en-9-one.

8. ±16,16-dimethyl-3-oxa-1,11β,15R-trihydroxyprost-13E-en-9-one.

9. ±16,16-dimethyl-3-oxa-1,11β,15R-trihydroxy-8,12-bis isoprost-13E-en-9-one.

10. A compound as defined by claim 1 wherein R is cycloalkyl of 5 to 7 carbon atoms.

11. 16,20-methano-3-oxa-1,11α,15R-trihydroxyprost-13E-en-9-one.

12. 16,20-methano-3-oxa-1,11β,15R-trihydroxy-8,12-bis isoprost-13E-en-9-one.

* * * * *

UNITED STATES PATENT AND TRADEMARK OFFICE
CERTIFICATE OF CORRECTION

PATENT NO. : 4,158,018
DATED : June 12, 1979
INVENTOR(S) : Harold C. Kluender

Page 1 of 3

It is certified that error appears in the above-identified patent and that said Letters Patent are hereby corrected as shown below:

Column 1, Line 55;  Change "prostaglandins" to -- prostaglandin --

Column 3, Line 54-57;  delete the formula and insert $$-- [Lig]_x \; Li^+ Cu^- \begin{smallmatrix} -- R^r \\ -- R^t \end{smallmatrix} \quad --$$

Column 7, Line 22;  Change "t-butyldimethylsily" to --t-butyldimethylsilyl --

Column 9, Lines 2-12  Change $$\text{"} \quad \begin{array}{c} Li \diagup\!\!\!\diagdown\!\!\!\diagup^{R^2}_{\substack{S \\ OR^3}} \\ 14 \; \downarrow \\ [Lig]_x CuR^r \\ 15 \end{array} \text{"} \quad \text{to}$$

$$-- \quad \begin{array}{c} Li \diagup\!\!\!\diagdown\!\!\!\diagup^{R^2}_{\substack{S \\ OR^3}} \\ [Lig]_x CuR^r \xrightarrow{14} \\ 15 \quad \downarrow \end{array} \quad --$$

UNITED STATES PATENT AND TRADEMARK OFFICE
CERTIFICATE OF CORRECTION

PATENT NO. : 4,158,018
DATED : June 12, 1979            Page 2 of 3
INVENTOR(S) : Harold C. Kluender It is certified that error appears in the above-identified patent and that said Letters Patent are hereby corrected as shown below:

Column 9,     Lines 13-16     Change "$\underset{12}{\overset{16\downarrow}{\phantom{X}}}$" to -- $12\!\!-\!\!\overset{16\downarrow}{\phantom{X}}$ --

Column 9,     Lines 44-50;    Change

" 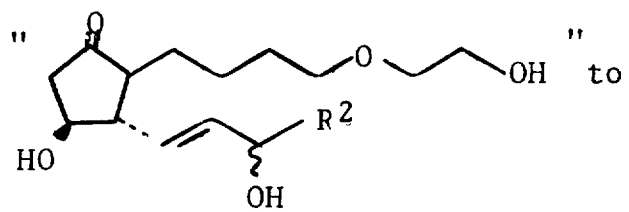 " to

-- 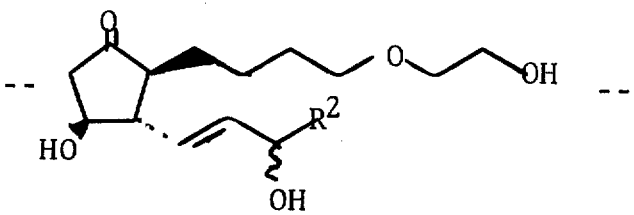 --

UNITED STATES PATENT AND TRADEMARK OFFICE
CERTIFICATE OF CORRECTION

PATENT NO. : 4,158,018
DATED : June 12, 1979    Page 3 of 3
INVENTOR(S) : Harold C. Kluender It is certified that error appears in the above-identified patent and that said Letters Patent are hereby corrected as shown below:

Column 16,    Line 64;    Change " 3,86" to --3.86--

Column 22,    Line 40;    Change "TR-5649" to
-- TR-4649 --

Signed and Sealed this

Twenty-fifth Day of September 1979

[SEAL]

Attest:

Attesting Officer

LUTRELLE F. PARKER
Acting Commissioner of Patents and Trademarks